US012761395B2

(12) United States Patent
Iwahori et al.

(10) Patent No.: US 12,761,395 B2
(45) Date of Patent: Oct. 13, 2026

(54) NON-TRANSITORY COMPUTER READABLE MEDIUM AND ESTIMATION METHOD

(71) Applicant: FURUNO ELECTRIC CO., LTD., Hyogo (JP)

(72) Inventors: Taiki Iwahori, Hyogo (JP); Masahiro Minowa, Hyogo (JP)

(73) Assignee: FURUNO ELECTRIC CO., LTD., Hyogo (JP)

( * ) Notice: Subject to any disclaimer, the term of this patent is extended or adjusted under 35 U.S.C. 154(b) by 389 days.

(21) Appl. No.: 18/480,491

(22) Filed: Oct. 3, 2023

(65) Prior Publication Data

US 2024/0027649 A1 Jan. 25, 2024

Related U.S. Application Data

(63) Continuation of application No. PCT/JP2022/009542, filed on Mar. 4, 2022.

(30) Foreign Application Priority Data

May 11, 2021 (JP) ................................ 2021-080522

(51) Int. Cl.
*G01W 1/10* (2006.01)
*G01N 22/00* (2006.01)
*G01N 33/18* (2006.01)

(52) U.S. Cl.
CPC .............. *G01W 1/10* (2013.01); *G01N 22/00* (2013.01); *G01N 33/18* (2013.01)

(58) Field of Classification Search
CPC ........... G01W 1/10; G01W 1/08; G01W 1/14; G01N 22/00; G01N 33/18; G06N 3/08; G06N 20/00; Y02A 90/10
See application file for complete search history.

(56) References Cited

U.S. PATENT DOCUMENTS

2008/0169975 A1* 7/2008 Yee ........................ G01S 13/50 342/26 R
2011/0218734 A1* 9/2011 Solheim .................. G01W 1/10 702/3

(Continued)

FOREIGN PATENT DOCUMENTS

CN 107356554 A * 11/2017 ........... G01N 21/359
CN 111060992 4/2020

(Continued)

OTHER PUBLICATIONS

I. A. Berezin et al., "Comparison of Ground-Based Microwave Measurements of Precipitable Water Vapor with Radiosounding Data", Atmospheric and Oceanic Optics, Jun. 15, 2016, pp. 274-281, vol. 29, No. 3.

(Continued)

*Primary Examiner* — Lal Ce Mang
(74) *Attorney, Agent, or Firm* — JCIPRNET

(57) ABSTRACT

Provided is a generation method for a learning model that can efficiently estimate altitude-by-altitude water vapor densities or precipitable water amounts. According to the present invention, a generation method for a learning model involves: acquiring training data that includes first measurement data measured by a microwave radiometer and altitude-by-altitude water vapor densities or precipitable water amounts obtained from second measurement data measured by a radiosonde: and, on the basis of the acquired training data, generating a learning model that, when first measurement data has been inputted, outputs altitude-by-altitude water vapor densities or precipitable water amounts.

21 Claims, 13 Drawing Sheets

(56) References Cited

U.S. PATENT DOCUMENTS

| | | | | |
|---|---|---|---|---|
| 2017/0131435 | A1 | 5/2017 | Peacock et al. | |
| 2020/0132884 | A1 * | 4/2020 | Rothenberg | G06N 5/04 |
| 2021/0041299 | A1 * | 2/2021 | Solheim | G06V 10/143 |

FOREIGN PATENT DOCUMENTS

| | | | | | |
|---|---|---|---|---|---|
| CN | 111220986 | | | 6/2020 | |
| CN | 111458769 | | | 7/2020 | |
| CN | 111638565 | | | 9/2020 | |
| CN | 112232554 | | | 1/2021 | |
| CN | 112462369 | | | 3/2021 | |
| JP | H0829546 | | | 2/1996 | |
| JP | 2010060444 | | | 3/2010 | |
| JP | 2019211342 | | | 12/2019 | |
| JP | 2019211342 | A | * | 12/2019 | Y02A 90/10 |
| WO | 2020230501 | | | 11/2020 | |
| WO | 2022014229 | | | 1/2022 | |

OTHER PUBLICATIONS

"International Search Report (Form PCT/ISA/210) of PCT/JP2022/009542", mailed on May 10, 2022, with English translation thereof, pp. 1-6.

* cited by examiner

| Time | Radio field intensity from black body[dB] (Calibrating observation data) | Radio field intensity from sky[dB] (Sky observation data) | Temperature | Humidity | Air pressure | Amount of rainfall |
|---|---|---|---|---|---|---|
| 2021:mm:dd:hh:m1 | ch01:bb1<br>ch02:bb2<br>ch03:bb3<br>·<br>·<br>ch40:bbx | ch01:sky1<br>ch01:sky2<br>ch01:sky3<br>·<br>·<br>ch40:skyx | TT | hh | PP | VV |
| 2021:mm:dd:hh:m2 | · | · | · | · | · | · |
| 2021:mm:dd:hh:m3 | · | · | · | · | · | · |
| 2021:mm:dd:hh:m4 | · | · | · | · | · | · |
| · | · | · | · | · | · | · |
| · | · | · | · | · | · | · |

FIG. 3

< Multiple-spot multiple-view screen >

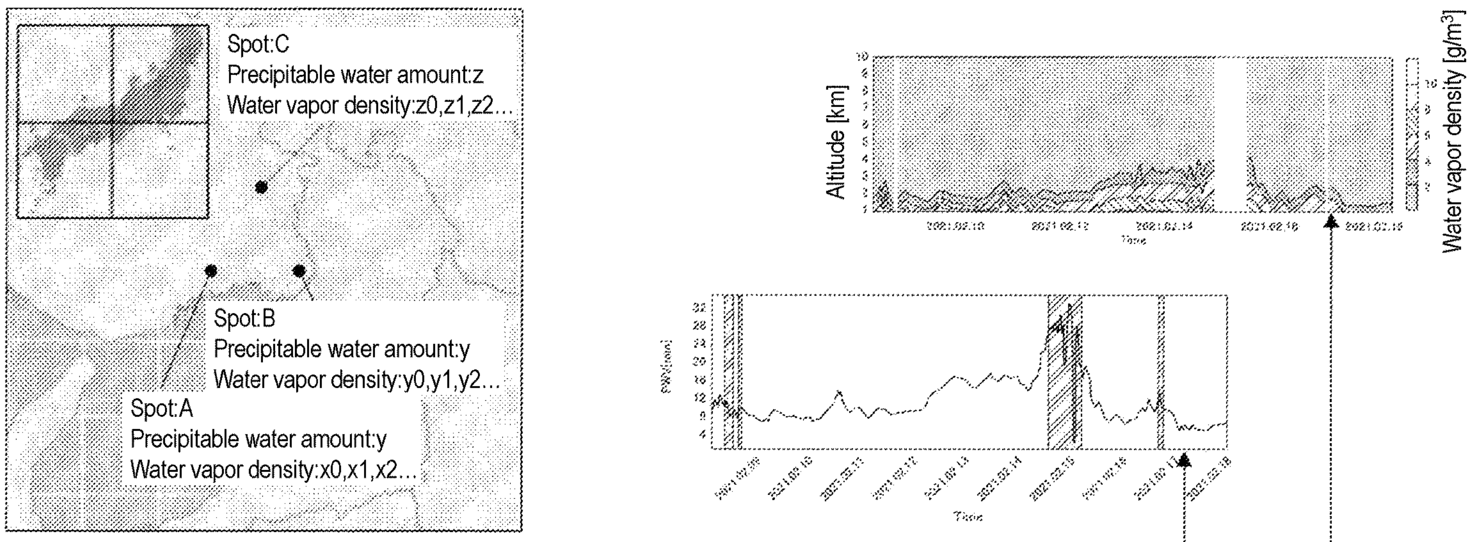

| Spot name | Address | Radio field intensity (sky~bb) | Precipitable water amount | Altitude-by-altitude water vapor density (altitudinal water vapor distribution) | | | | Precipitable water amount change graph | Altitudinal water vapor distribution graph |
|---|---|---|---|---|---|---|---|---|---|
| | | | | 0[km] | 1[km] | 2[km] | ・・[km] | | |
| A | xxx | ch01:bb1<br>ch02:bb2<br>ch03:bb3<br>・<br>・<br>ch40:bbx | x | x0 | x1 | x2 | x・ | [click] | [click] |
| B | yyy | | ・ | ・ | ・ | ・ | ・ | ・ | ・ |
| C | zzz | ・ | ・ | ・ | ・ | ・ | ・ | ・ | ・ |
| ・ | ・ | ・ | ・ | ・ | ・ | ・ | ・ | ・ | ・ |

FIG. 14

NON-TRANSITORY COMPUTER READABLE MEDIUM AND ESTIMATION METHOD

CROSS-REFERENCE TO RELATED APPLICATION

The present application is a continuation of PCT/JP2022/009542, filed on Mar. 4, 2022, and is related to and claims priority from Japanese patent application no. 2021-080522, filed on May 11, 2021. The entire contents of the aforementioned application are hereby incorporated by reference herein.

TECHNICAL FIELD

The disclosure relates to a generation method for a learning model, a non-transitory computer readable medium, an estimation method, and an estimation device.

BACKGROUND

It is known that a GNSS receiver, a microwave radiometer, and the like are used for observation of a precipitable water amount, that is, water vapor observation. Water vapor observation using a global navigation satellite system (GNSS) receiver uses radio waves of a plurality of frequencies radiated from satellites. When radio waves of two or more different frequencies radiated from four or more satellites can be received, it is possible to ascertain a delay of radio waves. The delay of radio waves corresponds to an amount of water vapor and enables observation of the amount of water vapor (for example, Japanese Patent Laid-Open No. 2010-60444). A rainfall prediction system described in Patent Literature 1 calculates a precipitable water amount based on a zenith atmosphere delay calculated from received GPS (GNSS) data and orbit information of satellites.

However, since the rainfall prediction system described in Patent Literature 1 calculates the precipitable water amount based on the GNSS data and requires orbit information of satellites, it is difficult to improve a temporal resolution for calculating the precipitable water amount. Altitude-by-altitude water vapor densities cannot be calculated from GNSS data.

The disclosure provides a generation method for a learning model or the like that can efficiently estimate altitude-by-altitude water vapor densities or a precipitable water amount.

SUMMARY

An aspect of the disclosure provides a non-transient computer-readable recording medium, recording a program causing a computer to preform: acquiring first measurement data measured by a microwave radiometer; and outputting altitude-by-altitude water vapor densities or a precipitable water vapor by inputting the first measurement data to a trained model which outputs the altitude-by-altitude water vapor densities or the precipitable water vapor amount when the first measurement data is input.

According to an embodiment of the disclosure, in the non-transient computer-readable recording medium, the first measurement data may include a radio wave intensity for each of a plurality of frequencies.

According to an embodiment of the disclosure, in the non-transient computer-readable recording medium, a dimension reduction process may be performed on the radio wave intensity for each of the plurality of frequencies included in the first measurement data, and the first measurement data including the radio wave intensity subjected to the dimension reduction process may be input to the trained model.

According to an embodiment of the disclosure, in the non-transient computer-readable recording medium, the trained model may be trained using training data including the altitude-by-altitude water vapor densities or the precipitable water vapor acquired from second measurement data measured by a radiosonde and the first measurement data.

According to an embodiment of the disclosure, in the non-transient computer-readable recording medium, the training data may further include climatological data including temperature, humidity, air pressure, or rainfall at a spot at which the microwave radiometer is installed. The non-transient computer-readable recording medium may further include: outputting the altitude-by-altitude water vapor densities or the precipitable water amount by inputting the first measurement data and the climatological data to the trained model.

According to an embodiment of the disclosure, in the non-transient computer-readable recording medium, a plurality of pieces of the first measurement data measured at a plurality of time points by the microwave radiometer may be acquired. The non-transient computer-readable recording medium may further include: generating change information of an altitudinal water vapor distribution based on the respective altitude-by-altitude water vapor densities at the plurality of time points output from the trained model; and outputting the change information of the altitudinal water vapor distribution.

According to an embodiment of the disclosure, in the non-transient computer-readable recording medium, a plurality of pieces of the first measurement data measured at a plurality of time points by the microwave radiometer may be acquired. The non-transient computer-readable recording medium may further include: generating change information of a precipitable water vapor based on the precipitable water vapor at the plurality of time points output from the trained model; and outputting the change information of the precipitable water amount.

According to an embodiment of the disclosure, in the non-transient computer-readable recording medium, first measurement data for each spot measured by the respective microwave radiometers installed in a plurality of spots may be acquired. The non-transient computer-readable recording medium may further include: outputting the altitude-by-altitude water vapor densities or the precipitable water vapor at each of the plurality of spots by inputting the first measurement data for each spot to the trained model.

According to an embodiment of the disclosure, in the non-transient computer-readable recording medium, map information for identifying the plurality of spots at which the plurality of microwave radiometers is installed may be acquired. The non-transient computer-readable recording medium may further include: superimposing the altitude-by-altitude water vapor densities or the precipitable water vapor at each of the plurality of spots in the map information.

According to an embodiment of the disclosure, in the non-transient computer-readable recording medium, climatological data including temperature, humidity, air pressure, or rainfall at each of the plurality of spots at which the plurality of microwave radiometers is installed may be acquired. The non-transient computer-readable recording medium may further include: inputting the first measurement data and the climatological data for each of the plurality of spots to the trained model.

According to an embodiment of the disclosure, in the non-transient computer-readable recording medium, the trained model may be trained using training data including the altitude-by-altitude water vapor densities or the precipitable water vapor acquired from second measurement data measured by a radiosonde and the first measurement data.

According to an embodiment of the disclosure, in the non-transient computer-readable recording medium, the training data may further include climatological data including temperature, humidity, air pressure, or rainfall at a spot at which the microwave radiometer is installed. The non-transient computer-readable recording medium may further include: outputting the altitude-by-altitude water vapor densities or the precipitable water amount by inputting the first measurement data and the climatological data to the trained model.

According to an embodiment of the disclosure, in the non-transient computer-readable recording medium, a plurality of pieces of the first measurement data measured at a plurality of time points by the microwave radiometer may be acquired. The non-transient computer-readable recording medium may further include: generating change information of an altitudinal water vapor distribution based on the respective altitude-by-altitude water vapor densities at the plurality of time points output from the trained model; and outputting the change information of the altitudinal water vapor distribution.

According to an embodiment of the disclosure, in the non-transient computer-readable recording medium, a plurality of pieces of the first measurement data measured at a plurality of time points by the microwave radiometer may be acquired. The non-transient computer-readable recording medium may further include: generating change information of a precipitable water vapor based on the precipitable water vapor at the plurality of time points output from the trained model; and outputting the change information of the precipitable water amount.

According to an embodiment of the disclosure, in the non-transient computer-readable recording medium, first measurement data for each spot measured by the respective microwave radiometers installed in a plurality of spots may be acquired. The non-transient computer-readable recording medium may further include: outputting the altitude-by-altitude water vapor densities or the precipitable water vapor at each of the plurality of spots by inputting the first measurement data for each spot to the trained model.

According to an embodiment of the disclosure, in the non-transient computer-readable recording medium, map information for identifying the plurality of spots at which the plurality of microwave radiometers is installed may be acquired. The non-transient computer-readable recording medium may further include: superimposing the altitude-by-altitude water vapor densities or the precipitable water vapor at each of the plurality of spots in the map information.

According to an embodiment of the disclosure, in the non-transient computer-readable recording medium, climatological data including temperature, humidity, air pressure, or rainfall at each of the plurality of spots at which the plurality of microwave radiometers is installed may be acquired. The non-transient computer-readable recording medium may further include: inputting the first measurement data and the climatological data for each of the plurality of spots to the trained model.

Another aspect of the disclosure provides processing circuitry configured to: acquire first measurement data measured by a microwave radiometer; and input the first measurement data to a trained model which outputs altitude-by-altitude water vapor densities or a precipitable water vapor when the first measurement data is input, and estimate the altitude-by-altitude water vapor densities or the precipitable water vapor.

Yet another aspect of the disclosure provides an estimation method performed by a computer. The estimation method includes: acquiring first measurement data measured by a microwave radiometer; and inputting the first measurement data to a learning model which outputs altitude-by-altitude water vapor densities or a precipitable water vapor when the first measurement data is input, and estimating the altitude-by-altitude water vapor densities or the precipitable water vapor.

BRIEF DESCRIPTION OF DRAWINGS

The illustrated embodiments of the subject matter will be best understood by reference to the drawings, wherein like parts are designated by like numerals throughout. The following description is intended only by way of example, and simply illustrates certain selected embodiments of devices, systems, and processes that are consistent with the subject matter as claimed herein.

FIG. 3 is an explanatory diagram illustrating an example of observation data from the microwave radiometer.

FIG. 14 is an explanatory diagram illustrating an example of an observation state at a plurality of spots (superimposed in map information).

DETAILED DESCRIPTION

According to the disclosure, it is possible to provide a generation method for a learning model or the like that can efficiently estimate altitude-by-altitude water vapor densities or a precipitable water amount.

First Embodiment

Figure 1:
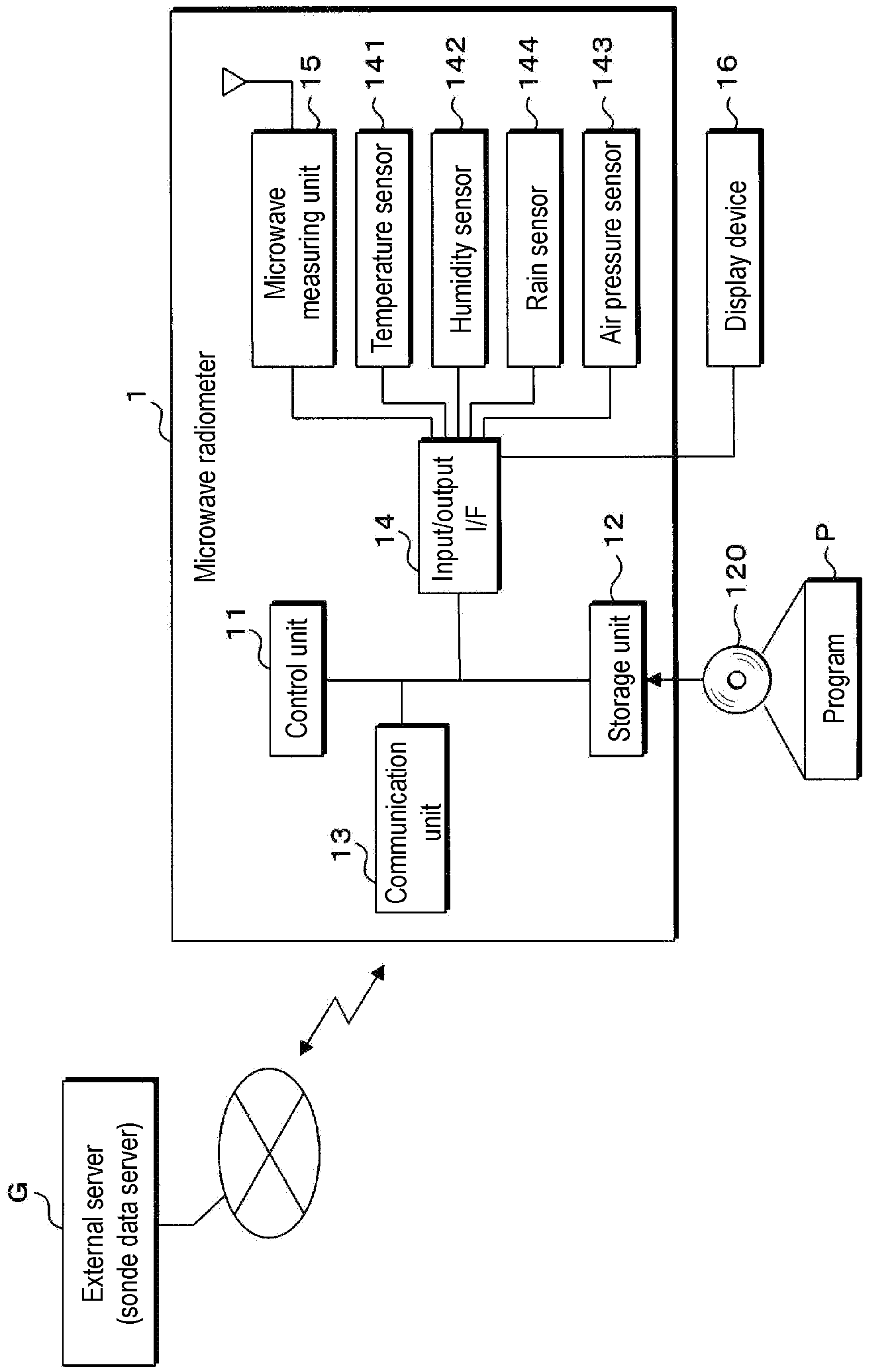
FIG. 1 is a block diagram illustrating an example of a configuration of a microwave radiometer according to a first embodiment.

Hereinafter, an embodiment of the disclosure will be described. FIG. 1 is a block diagram showing an example of a configuration of a microwave radiometer 1 according to a first embodiment. The microwave radiometer 1 is communicatively connected to an external server G (a sonde data server) in which altitudinal temperature, humidity, and air pressure (sonde data) measured by a radiosonde are stored via an external network such as the Internet.

The microwave radiometer 1 generates training data based on sonde data such as altitude-by-altitude temperatures acquired from the external server G and radio field intensities of microwaves measured at an observation spot at which a radiosonde for observing the sonde data is released. The sonde data such as altitude-by-altitude temperatures acquired from the external server G corresponds to second measurement data, and the radio field intensities of microwaves measured by the microwave radiometer 1 at the observation spot at which the radiosonde is released corresponds to first measurement data.

Although details will be described later, the microwave radiometer 1 serves as a learning model generation device that trains, for example, parameters of a neural network using the generated training data and generating a precipitable water amount model 121, an altitudinal water vapor distribution model 122, or both models. The microwave radiometer 1 serves as a precipitable water amount estimation device (a water vapor observation device) that estimates a precipitable water amount in the sky in the vertical direction at a spot at which the microwave radiometer 1 is installed by inputting radio field intensities of microwaves measured at the spot to the precipitable water amount model 121. The microwave radiometer 1 serves as an altitudinal water vapor distribution estimation device (a water vapor observation device) that estimates altitude-by-altitude water vapor densities (an altitudinal water vapor distribution) in the sky in the vertical direction at the spot at which the microwave radiometer 1 is installed by inputting the radio field intensities of microwaves measured at the spot to the generated altitudinal water vapor distribution model 122.

The microwave radiometer 1 generates training data for generating a learning model (the precipitable water amount model 121 or the altitudinal water vapor distribution model 122) based on the measured radio field intensities of microwaves, but is not limited thereto. The microwave radiometer 1 may generate the learning model using training data which is generated based on temperature, humidity, air pressure, and rainfall at the spot at which the microwaves have been measured in addition to the radio field intensities of microwaves.

The microwave radiometer 1 generates input data for generating a learning model (the precipitable water amount model 121 or the altitudinal water vapor distribution model 122) based on the measured radio field intensities of microwaves, but is not limited thereto. The microwave radiometer 1 may acquire a precipitable water amount or an altitudinal water vapor distribution by inputting the input data which is generated based on temperature, humidity, air pressure, and rainfall at the spot at which the microwaves have been measured to the learning model (the precipitable water amount model 121 or the altitudinal water vapor distribution model 122) in addition to the radio field intensities of microwaves.

The external server G is constituted by, for example, a cloud server connected to the Internet or the like and is managed by a public institution (the Japan Meteorological Agency) that operates radiosondes. In the external server G, sonde data such as altitudinal temperature, humidity (relative humidity), and air pressure measured (observed) by the radiosondes released at observation spots is stored in correlation with the observation spots and the observation date and time. The sonde data can be acquired by accessing the external server G.

The microwave radiometer 1 includes a microwave measuring unit 15 configured to measure microwaves radiated from the atmosphere and a temperature sensor 141, a humidity sensor 142, an air pressure sensor 143, and a rain sensor 144 for acquiring climatological data at the spot at which the microwave radiometer 1 is installed. The microwave radiometer 1 further includes a control unit 11 (which is also referred to as a processing circuitry), a storage unit 12, a communication unit 13, and an input/output I/F 14 for processing or handling various types of measurement data acquired by the sensor group.

The microwave measuring unit 15 includes, for example, a radio wave window, a black body, a receiving horn, and an AD conversion circuit, receives microwaves input through the radio wave window using the receiving horn, and converts the received microwaves to radio field intensities (dB) for frequencies using the AD conversion circuit. In this embodiment, for example, microwaves of about 40 channels (frequencies) in the range of from 16 GHz to 26 GHz are measured, and a radio field intensity (dB) of each of the 40 channels is measured. The peak of the radio field intensities of radio waves radiated from water vapor and cloud water in the sky appears at 22 GHz, and it is possible to improve identification accuracy of a water vapor component and a cloud water component by acquiring (measuring) the radio field intensities of the about 40 channels (frequencies) in the range of from 16 GHz to 26 GHz.

The microwave radiometer 1 alternately acquires microwaves radiated from a black body and microwaves radiated from the sky by periodically causing the black body to pass through the reception range of the receiving horn using a motor or the like and periodically positioning the black body to cover the receiving horn with respect to the sky. The black body is constituted, for example, by vantablack and corresponds to a reference radio wave absorber. In this way, the microwave radiometer 1 repeatedly performs a process of measuring microwaves from the reference radio wave absorber (the black body), for example, for 10 seconds and then measuring microwaves from the sky, for example, for 10 seconds. The microwave radiometer 1 acquires a difference value (sky−bb [dB]) obtained by subtracting the radio field intensity (bb [dB]) of the microwaves from the black body from the radio field intensity (sky [dB]) of the microwaves from the sky as the radio field intensity of the measured microwaves for each of the 40 channels (frequencies).

In measuring (observing) microwaves from the black body and the sky, the microwave radiometer 1 may automatically calibrate linearity of analog instruments or the like (detector calibration). The microwave radiometer 1 may switch an attenuator connected to the receiving horn, ascertain whether a digital value obtained by conversion in the AD conversion circuit is linear with respect to a pre-conversion analog value (both are in a proportional relationship based on an ideal straight line), and perform linearity calibration of an analog system when the digital value obtained by AD conversion exceeds an allowable error range.

The temperature sensor 141 is constituted, for example, by a thermistor and detects air temperature at the spot at which the microwave radiometer 1 is installed. The humidity sensor 142 is, for example, a capacitance-change or resistance-change electric sensor, detects an amount of water vapor in the ambient air of the spot at which the microwave radiometer 1 is installed, and converts the detected amount to an electrical signal. The air pressure sensor 143 is constituted, for example, by a pressure receiving device and detects air pressure (atmospheric pressure) at the spot at which the microwave radiometer 1 is installed. The rain sensor 144 is, for example, a sensor that linearly changes a voltage value which is output based on an amount of rainfall, detects an amount of rainfall at the spot at which the microwave radiometer 1 is installed, and converts the detected amount to an electrical signal.

The microwave measuring unit 15, the temperature sensor 141, the humidity sensor 142, the air pressure sensor 143, and the rain sensor 144 are communicatively connected to the control unit 11 and the storage unit 12, for example, via the input/output I/F 14 or an internal bus. Measurement data measured by the microwave measuring unit 15, the temperature sensor 141, and the like is correlated with time information indicating a time point at which it is measured and is stored, for example, as time-series data in a table form (see FIG. 3) in the storage unit 12.

The control unit 11 includes an arithmetic processing unit having a timer function such as one or more central processing units (CPUs), micro-processing units (MPUs), or graphics processing units (GPUs) and performs various information processes, a control process on the microwave measuring unit 15, and the like by reading and executing a program P stored in the storage unit 12.

The storage unit 12 includes a volatile storage area such as a static random access memory (SRAM), a dynamic random access memory (DRAM), or a flash memory and a non-volatile storage area such as an EEPROM or a hard disk. The program P and data which is referred to at the time of processing are stored in the storage unit 12 in advance. The program P stored in the storage unit 12 may be a program P (a program product) which is read from a recording medium 120 readable by the control unit 11 and which is stored therein. A program P (a program product) may be downloaded from an external computer (not illustrated) connected to a communication network which is not illustrated and stored in the storage unit 12. Actual files constituting learning models (the precipitable water amount model 121 and the altitudinal water vapor distribution model 122) are stored in the storage unit 12. These actual files may constitute a part of the program P.

The communication unit 13 is a communication module or a communication interface for communicating with an external server G (a sonde data server) in a wired or wireless manner and includes, for example, a local-area radio communication module such as Wi-Fi (registered trademark) or Bluetooth (registered trademark) or a wide-area radio communication module such as 4G or 5G. The control unit 11 communicates with the external server G via an external network such as the Internet using the communication unit 13.

The input/output I/F 14 includes, for example, a communication interface based on a communication protocol such as USB or a connector for connection to the internal bus. The microwave measuring unit 15, the temperature sensor 141, the humidity sensor 142, the air pressure sensor 143, and the rain sensor 144 may be connected to the input/output I/F 14. A display device 16 such as a liquid crystal display may be additionally connected to the input/output I/F 14.

In this embodiment, the microwave radiometer 1 includes the microwave measuring unit 15, various sensors, and the control unit 11 for performing data processing, but is not limited thereto. The control unit 11 or the like for performing data processing may be provided in a computer separate from the microwave radiometer 1, the microwave radiometer 1 and the computer may be communicatively connected, and the computer may perform generation of learning models and estimation using the learning models by processing various types of data measured by the microwave radiometer 1. The computer may acquire (receive) observation data (radio field intensities and climatological data) from microwave radiometers 1 installed at a plurality of observation spots which are observed by radiosondes and generate training data based on the observation data and the sonde data for each observation spot. The learning models (a precipitable water amount model and an altitudinal water vapor distribution model) having learned the observation data and the sonde data at the plurality of observation spots in this way may be applied to the individual microwave radiometers 1, and the individual microwave radiometers 1 may perform an estimation process using the learning models.

Figure 2:
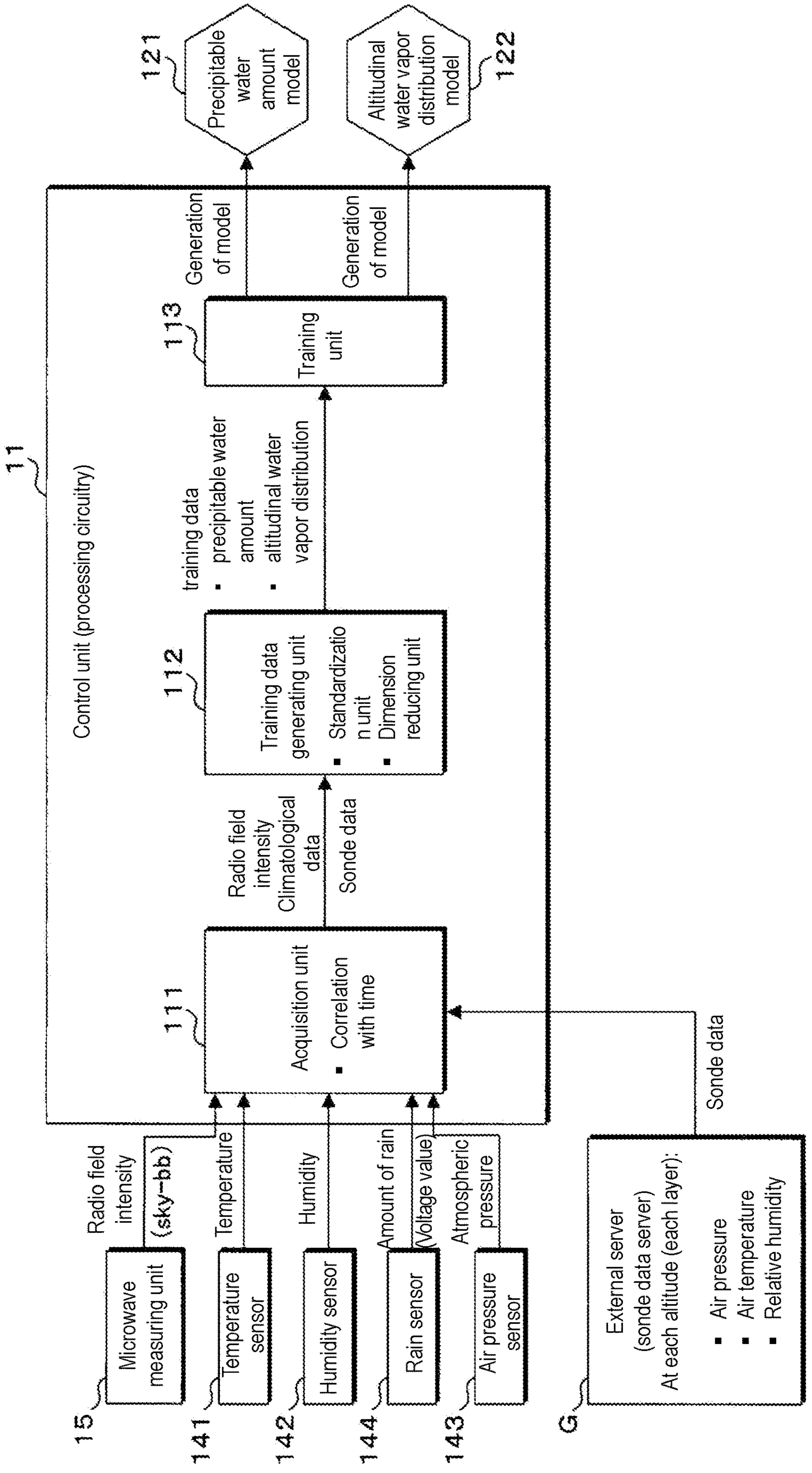
FIG. 2 is a functional block diagram illustrating functional units (at the time of learning) included in a control unit of the microwave radiometer.

FIG. 2 is a functional block diagram illustrating functional units (at the time of learning) included in the control unit 11 of the microwave radiometer 1. The control unit 11 of the microwave radiometer 1 serves as an acquisition unit 111, a training data generating unit 112, and a training unit 113 by executing a program P stored in the storage unit 12.

The acquisition unit 111 acquires, for example, radio field intensities (first measurement data) in each of about 40 channels (frequencies) in the range of from 16 GHz to 26 GHz from the microwave measuring unit 15. The acquisition unit 111 acquires measured values (climatological data) such as temperature output from the temperature sensor 141, the humidity sensor 142, the air pressure sensor 143, and the rain sensor 144. The acquisition unit 111 acquires the radio field intensities (first measurement data) and the measured values (climatological data) such as temperature, the microwave radiometer 1 is installed in a spot (area) in which observation by a radiosonde is performed. A time period in which the acquisition unit 111 acquires the radio field intensities (first measurement data) and the measured values (climatological data) is the same as a time period in which observation by the radiosonde is performed. That is, the radio field intensities (first measurement data) and the measured values (climatological data) such as temperature acquired by the acquisition unit 111 geographically and temporally correspond to sonde data observed (measured) by the radiosonde.

FIG. 3 is an explanatory diagram illustrating an example of observation data from the microwave radiometer 1. The acquisition unit 111 correlates the acquired radio field intensities (first measurement data) and the measured values (climatological data) such as temperature with a time point (a measurement time point) at which the data has been acquired and stores the correlated data, for example, in a table format (an observation data table) in the storage unit 12. The observation data table includes time, a radio field intensity from a black body, a radio field intensity from the sky, temperature, humidity, air pressure, and rainfall as management items (fields).

In the management item (field) of time, date and time information indicating a date and time indicating of an observation time point (an acquisition time point) of observation data (radio field intensities and climatological data) is stored. In the management item (field) of a radio field intensity from a black body, radio field intensities of about 40 channels (frequencies) in the range of from 16 GHz to 26 GHz radiated from the black body are stored as calibrating observation data. In the management item (field) of radio field intensity from the sky, radio field intensities of about 40 channels (frequencies) in the range of from 16 GHz to 26 GHz radiated from the sky are stored as sky observation data.

Figure 4:
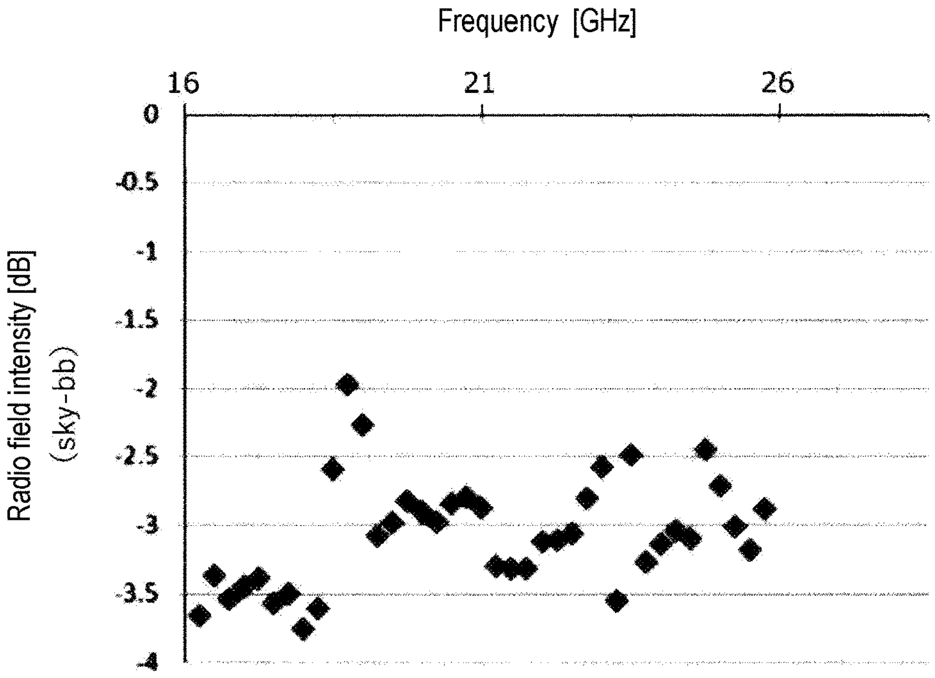
FIG. 4 is an explanatory diagram illustrating an example of a radio field intensity of microwaves (sky-bb) included in the observation data.

In this embodiment, the radio field intensities from the black body and the sky are stored in a table format, but is not limited thereto. A difference value (sky−bb) obtained by subtracting the radio field intensity (bb) of the black body from the radio field intensity (sky) of the sky may be stored. FIG. 4 is an explanatory diagram illustrating an example of the radio field intensity of microwaves (sky−bb) included in the observation data. In the explanatory diagram, the vertical axis represents the radio field intensity of the difference value (sky−bb) and the horizontal axis represents a channel (frequency). Since the black body (the reference radio wave absorber) is at the normal temperature (high temperature) and has a higher radiation intensity than that of the sky, the difference value (sky−bb) obtained by subtracting the radio field intensity (bb) of the black body from the radio field intensity (sky) of the sky has, for example, a negative value of from 0 dB to about −5 dB.

In the management item (field) of temperature, the air temperature at the spot at which the microwave radiometer 1 is installed is stored. In the management item (field) of humidity, absolute humidity or relative humidity at the spot at which the microwave radiometer 1 is installed is stored. In the management item (field) of air pressure, the air pressure (atmospheric pressure) at the spot at which the microwave radiometer 1 is installed is stored. In the management item (field) of time, a voltage value indicating an amount of rainfall at the spot at which the microwave radiometer 1 is installed is stored.

The acquisition unit 111 acquires altitude-by-altitude temperatures, humidity, and air pressure (sonde data) measured by the radiosonde from the external server G. As described above, the sonde data and the observation data (the radio field intensities and the climatological data) geographically and temporally correspond to each other.

The training data generating unit 112 generates training data for generating (training) the precipitable water amount model 121 and the altitudinal water vapor distribution model 122 based on the observation data (the radio field intensities and the climatological data) measured by the microwave radiometer 1 and the sonde data acquired from the external server G. The training data includes question data generated based on the observation data (the radio field intensities and the climatological data) and answer data generated based on the sonde data. The radio field intensity is expressed as the difference value (sky−bb) obtained by subtracting the radio field intensity (bb) of the black body from the radio field intensity (sky) of the sky.

The observation data (the radio field intensities and the climatological data) measured by the microwave radiometer 1 temporally corresponds to the sonde data. The training data generating unit 112 may generate question data based on a plurality of pieces of observation data (the radio field intensities and the climatological data) measured at a plurality of time points included in a time period in which the sonde data is observed (measured). The training data generating unit 112 may generate question data based on averaged, standardized, or normalized observation data (radio field intensities and climatological data) by performing an averaging process, a standardization process, or a normalization process on the observation data (the radio field intensities and the climatological data) at the plurality of time points. That is, the training data generating unit 112 may include a standardization unit for standardizing observation data or the like.

The training data generating unit 112 may perform a dimension reducing process on first measurement data including, for example, the radio field intensities of about 40 channels (frequencies) in the range of from 16 GHz to 26 GHz and generate question data based on the first measurement data subjected to the dimension reducing process. That is, the training data generating unit 112 may include a dimension reducing unit that performs the dimension reducing process on the observation data. The dimension reducing process may perform the dimension reduction, for example, using principal component analysis (PCA) on the radio field intensities at a plurality of frequencies and use a particular number of principal components subsequent to the first rank as the first measurement data for generating (training) a learning model. The dimension reducing process may set the particular number of principal components to be, for example, 3 and select a first principal component, a second principal component, and a third principal component. The principal component analysis is not limited to PCA, and may use an algorithm such as factor analysis, multiple factor analysis, autoencoder, independent component analysis, or non-negative matrix factor analysis.

In this embodiment, the training data generating unit 112 generates question data based on the radio field intensities and the climatological data (temperature, humidity, air pressure, and rainfall) measured by the microwave radiometer 1, but is not limited thereto. The training data generating unit 112 may generate question data based on only the radio field intensity measured by the microwave radiometer 1. Alternatively, the training data generating unit 112 may generate question data based on temperature, humidity, and air pressure in addition to the radio field intensity. That is, the training data generating unit 112 may generate question data based on some data included in the climatological data in addition to the radio field intensity.

The training data generating unit 112 calculates altitude-by-altitude water vapor density by differentiating a total amount of water vapor (1/g*((r[i]+r[i+1])/2*(P[i]−P[i+1]))) *0.1, "g=9.81 m/s^2, r=mixing ratio, P=air pressure") calculated using a known method in the altitudinal direction and calculates a precipitable water amount by integrating the altitude-by-altitude water vapor densities in the altitudinal direction. The altitude-by-altitude water vapor densities (altitudinal water vapor distribution) corresponds to answer data for generating (training) the altitudinal water vapor distribution model 122. The precipitable water amount corresponds to answer data for generating (training) the precipitable water amount model 121. The question data generated based on the observation data (the radio field intensities and the climatological data) is common data (question data) in generating (training) the precipitable water amount model 121 and the altitudinal water vapor distribution model 122.

The training data generating unit 112 generates training data for the altitudinal water vapor distribution model 122 for generating (training) the altitudinal water vapor distribution model 122 using the question data and the answer data including the altitude-by-altitude water vapor densities (altitudinal water vapor distribution) generated based on the sonde data. The training data generating unit 112 generates training data for the precipitable water amount model 121 for generating (training) the precipitable water amount model 121 using the question data and the answer data including the precipitable water amount generated based on the sonde data.

Figure 5:
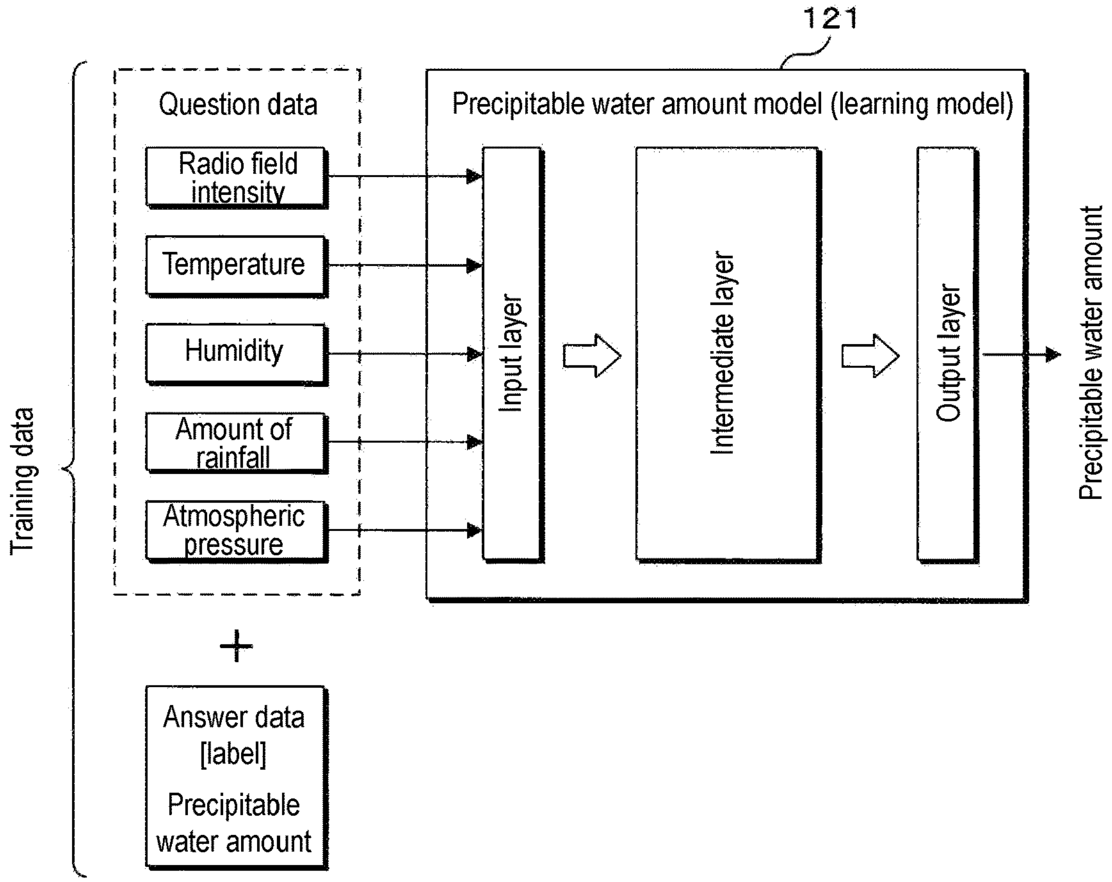
FIG. 5 is a diagram schematically illustrating an example of a method of generating a precipitable water amount model through machine learning.

FIG. 5 is a diagram schematically illustrating an example of a method of generating the precipitable water amount model 121 using machine learning. The training unit 113 trains a neural network using the training data for the precipitable water amount model 121 and generates the precipitable water amount model 121 with the observation data (the radio field intensities and the climatological data) as an input and with the precipitable water amount as an output. The neural network (the precipitable water amount model 121) trained using the training data is assumed to be used as a program P module which is a part of artificial intelligence software. The precipitable water amount model 121 is used by the microwave radiometer 1 including the control unit 11 (such as the CUP) and the storage unit 12 as described above and is performed in the microwave radiometer 1 having such arithmetic processing capability to constitute a neural network system.

The precipitable water amount model 121 is constituted, for example, by a deep neural network (DNN) and includes an input layer for receiving an input of observation data, an intermediate layer for extracting feature quantities of the observation data, and an output layer for outputting a precipitable water amount. The input layer includes a plurality of neurons for receiving an input of values such as radio field intensities or temperature included in the observation data and delivers the input values to the intermediate layer. The intermediate layer is defined using an activation function such as an ReLu function or a sigmoid function, includes a plurality of neurons for extracting feature quantities of the input values, and delivers the extracted feature quantities to the output layer. Parameters such as weighting factors and bias values in the activation function are optimized using an error back-propagation method. The output layer is constituted, for example, by a fully coupled layer and outputs a precipitable water amount based on the feature quantities output from the intermediate layer.

In this embodiment, the precipitable water amount model 121 is a DNN, but is not limited thereto and it may be a learning model constructed using another learning algorithm of a neural network other than the DNN, such as a recurrent neural network (RNN), a long-short term model (LSTM), a CNN, a support vector machine (SVM), a Bayesian network, linear regression, a regression tree, multiple regression, random forest, or ensemble. For example, when multiple regression including a plurality of types of variables is used, the precipitable water amount model 121 may be expressed by a transformation using polynomial regression. In this case, the transformation is defined by an inner product of vectors between the same number of unknown coefficients (S1 to Sn) as the number of dimensions (n) of observation data (the radio field intensities and the climatological data) subjected to principal component analysis and the observation data subjected to principal component analysis, and these coefficients (S1 to Sn) are calculated, for example, by fitting using a least square method.

Figure 6:
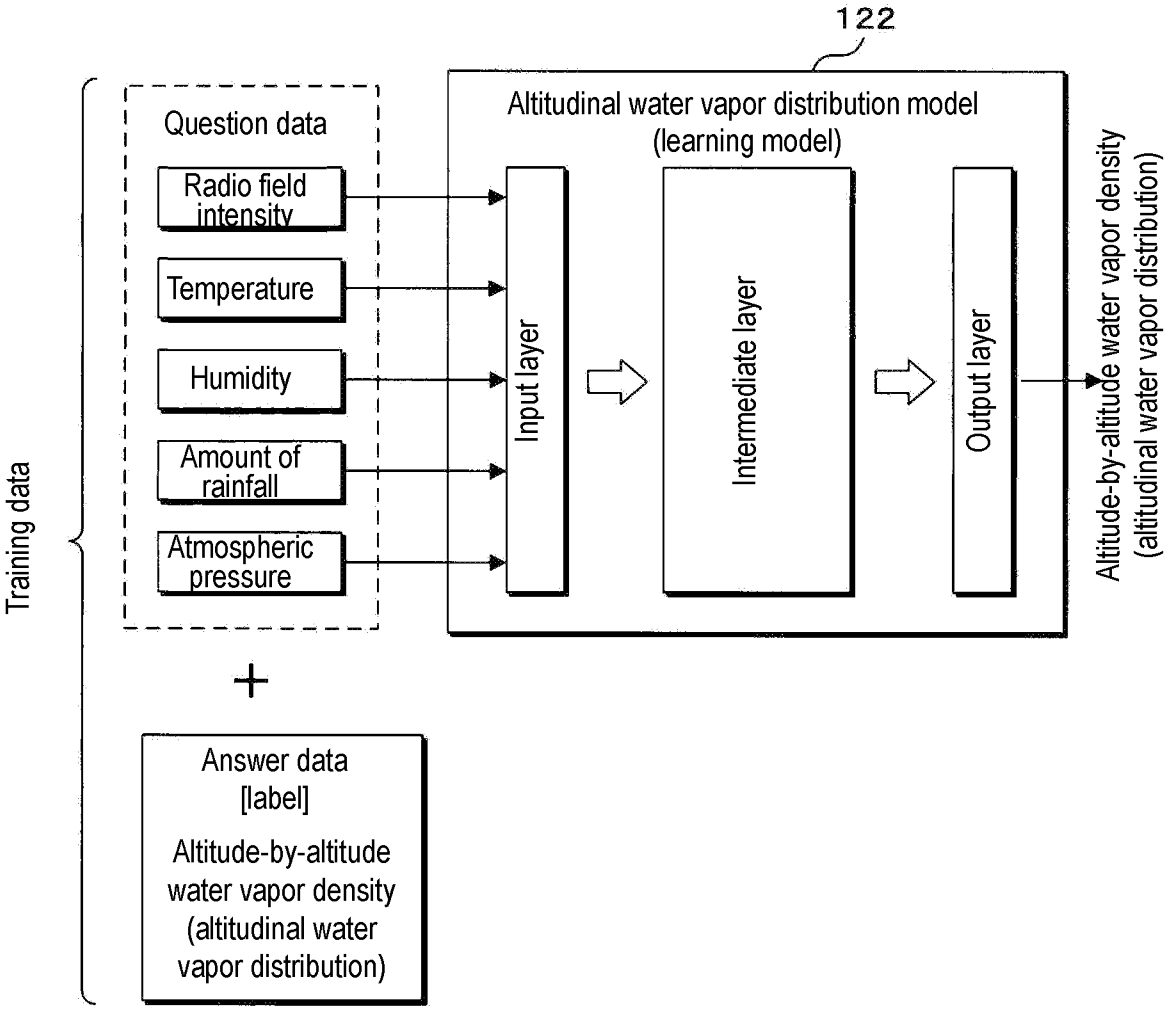
FIG. 6 is a diagram schematically illustrating an example of a method of generating an altitudinal water vapor distribution model through machine learning.

FIG. 6 is a diagram schematically illustrating an example of a method of generating the altitudinal water vapor distribution model 122 through machine learning. The training unit 113 trains a neural network using the training data for an altitudinal water vapor distribution model 122 and generates an altitudinal water vapor distribution model 122 with the observation data (the radio field intensities and the climatological data) as an input and with the altitudinal water vapor densities (the altitudinal water vapor distribution) as an output.

The altitudinal water vapor distribution model 122 is constituted, for example, by a DNN and includes an input layer for receiving an input of observation data, an intermediate layer for extracting feature quantities of the observation data, and an output layer for outputting an altitudinal water vapor distribution. Alternatively, the altitudinal water vapor distribution model 122 may be expressed by a transformation using polynomial regression using multiple regression including a plurality of types of variables. In this way, the altitudinal water vapor distribution model 122 has the same configuration as the precipitable water amount model 121, and the training unit 113 generates a altitudinal water vapor distribution model 122 in the same way as the precipitable water amount model 121.

Figure 7:
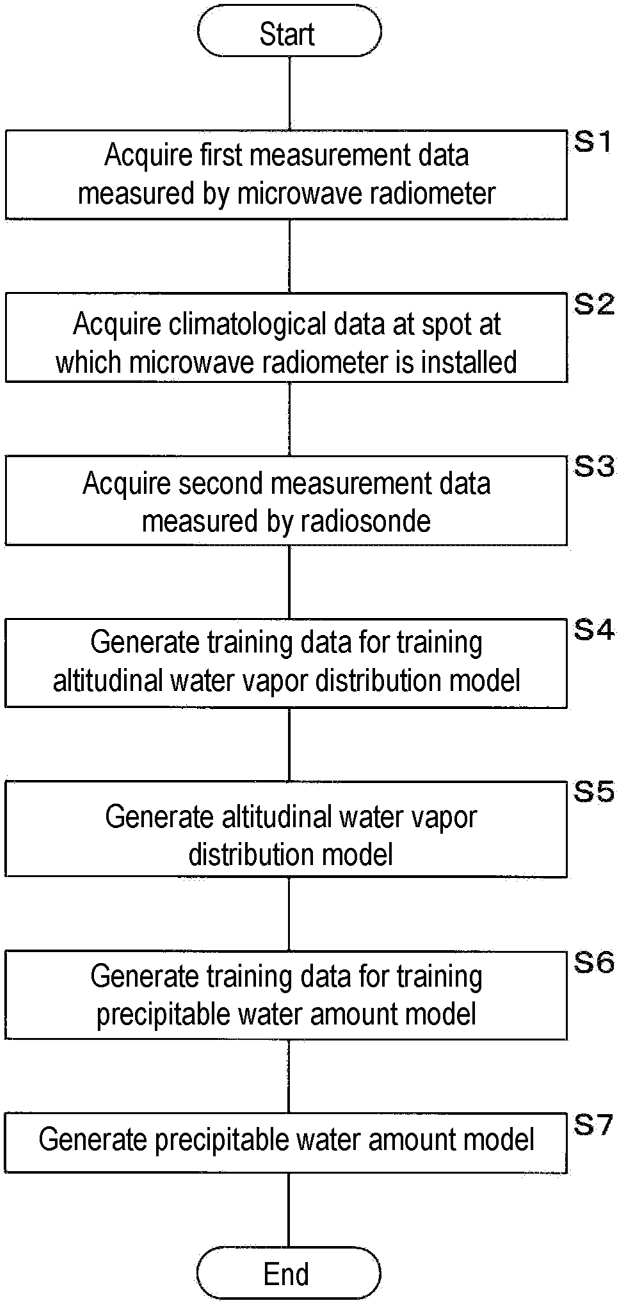
FIG. 7 is a flowchart illustrating an example of a routine (at the time of learning) which is performed by the control unit of the microwave radiometer.

FIG. 7 is a flowchart illustrating an example of a routine (at the time of learning) that is performed by the control unit 11 of the microwave radiometer 1. For example, the control unit 11 of the microwave radiometer 1 receives an operation from an operator via a keyboard connected to the input/output I/F 14 and performs the following processes based on the received operation.

The control unit 11 of the microwave radiometer 1 acquires first measurement data measured by the microwave radiometer 1 (the microwave measuring unit 15) (S1). For example, the control unit 11 of the microwave radiometer 1 acquires radio field intensities (first measurement data) in about 40 channels (frequencies) in the range of from 16 GHz to 26 GHz. The control unit 11 of the microwave radiometer 1 may use a difference value (sky−bb) obtained by subtracting a radio field intensity (bb) of a black body from a radio field intensity (sky) of the sky in each of the channels (frequencies) as the first measurement data.

The control unit 11 of the microwave radiometer 1 acquires climatological data of a spot at which the microwave radiometer 1 is installed (S2). The control unit 11 of the microwave radiometer 1 acquires measured values (climatological data) such as temperature or the like output from the temperature sensor 141, the humidity sensor 142, the air pressure sensor 143, and the rain sensor 144. The radio field intensities (first measurement data) and the measured values (climatological data) such as temperature geographically and temporally correspond to sonde data measured by a radiosonde. The acquisition of climatological data is not limited to acquisition from the sensors such as the temperature sensor 141 provided in the microwave radiometer 1, and the control unit 11 of the microwave radiometer 1 may acquire climatological data of the spot at which the microwave radiometer 1 is installed, for example, from a climatological data server connected to the Internet or the like via the communication unit 13.

The control unit 11 of the microwave radiometer 1 acquires second measurement data measured by the radiosonde (S3). The control unit 11 of the microwave radiometer 1 accesses the external server G (the sonde data server) via the communication unit 13 and acquires sonde data (second measurement data) including altitude-by-altitude temperatures, humidity, and air pressure measured by the radiosonde.

The control unit 11 of the microwave radiometer 1 generates training data for training the altitudinal water vapor distribution model 122 (a learning model) that outputs altitude-by-altitude water vapor densities based on the first measurement data, the climatological data, and the second measurement data (S4). The control unit 11 of the microwave radiometer 1 generates training data for the altitudinal water vapor distribution model 122 based on the observation data (the radio field intensities and the climatological data) measured by the microwave radiometer 1 and the sonde data acquired from the external server G. In generating the training data, the control unit 11 of the microwave radiometer 1 may perform a standardization process or a dimension reducing process on the observation data (the radio field intensities and the climatological data) at a plurality of time points.

The control unit 11 of the microwave radiometer 1 generates the altitudinal water vapor distribution model 122 (a learning model) by performing training using the training data (S5). The control unit 11 of the microwave radiometer 1 generates the altitudinal water vapor distribution model 122 (a learning model), for example, by training a neural network using the training data for the altitudinal water vapor distribution model 122.

The control unit 11 of the microwave radiometer 1 generates training data for training the precipitable water amount model 121 (a learning model) that outputs a precipitable water amount based on the first measurement data, the climatological data, and the second measurement data (S6). The control unit 11 of the microwave radiometer 1 generates training data for the precipitable water amount model 121 based on the observation data (the radio field intensities and the climatological data) measured by the microwave radiometer 1 and the sonde data acquired from the external server G. In generating the training data, the control unit 11 of the microwave radiometer 1 may perform a standardization process or a dimension reducing process on the observation data (the radio field intensities and the climatological data) at a plurality of time points.

The control unit 11 of the microwave radiometer 1 generates the precipitable water amount model 121 (a learning model) by performing training using the training data (S7). The control unit 11 of the microwave radiometer 1 generates the precipitable water amount model 121 (a learning model), for example, by training a neural network using the training data for the precipitable water amount model 121.

In this embodiment, the control unit 11 of the microwave radiometer 1 acquires the radio field intensities (first measurement data) and the climatological data as the observation data, but is not limited thereto. The control unit 11 of the microwave radiometer 1 may generate training data based on only the radio field intensities (the first measurement) or some of the climatological data such as temperature, humidity, and air pressure in addition to the radio field intensities (the first measurement data) and generate the precipitable water amount model 121 and the altitudinal water vapor distribution model 122.

After generating the learning models (the precipitable water amount model 121 and the altitudinal water vapor distribution model 122), the control unit 11 of the microwave radiometer 1 may re-acquire training data including the first measurement data and the second measurement data and re-train the learning models generated already based on the re-acquired training data. Accordingly, it is possible to further improve estimation accuracy of the learning models (the precipitable water amount model 121 and the altitudinal water vapor distribution model 122) Re-training of the learning models (the precipitable water amount model 121 and the altitudinal water vapor distribution model 122) is not limited to fine tuning or transfer learning of a learning model generated already, and the learning models may be regenerated by training non-trained neural network using training data in which the re-acquired training data is added to the previously used training data. The control unit 11 of the microwave radiometer 1 may re-training the generated learning model in operating the generated learning model. In this case, the control unit 11 of the microwave radiometer 1 may derive a difference between a precipitable water amount estimated using the learning model and a precipitable water amount calculated based on the sonde data and re-train the learning model when the difference is greater than a particular value.

Figure 8:
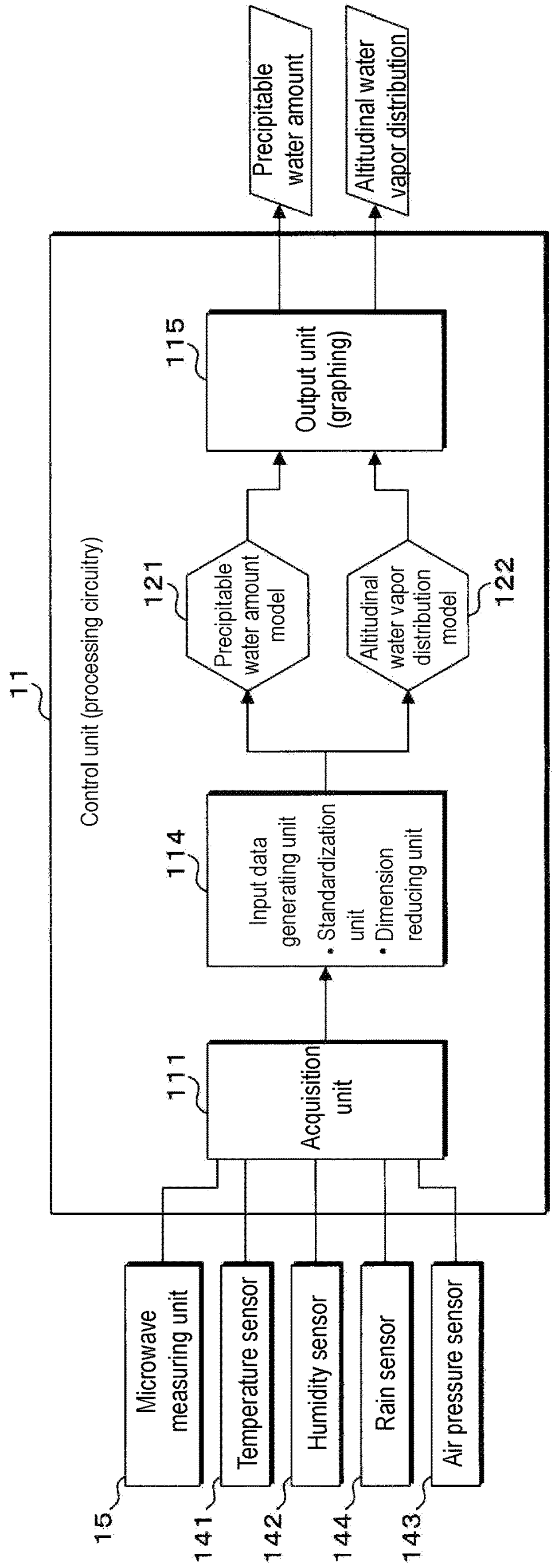
FIG. 8 is a functional block diagram illustrating functional units (at the time of operating) included in the control unit of the microwave radiometer.

FIG. 8 is a functional block diagram illustrating functional units (at the time of operating) included in the control unit 11 of the microwave radiometer 1. The control unit 11 of the microwave radiometer 1 serves as an acquisition unit 111, an input data generating unit 114, and an output unit 115 by executing a program P stored in the storage unit 12.

The acquisition unit 111 acquires, for example, a radio field intensity (first measurement data) in each of about 40 channels (frequencies) in the range of from 16 GHz to 26 GHz from the microwave measuring unit 15. The acquisition unit 111 acquires measured values (climatological data) such as temperature or the like output from the temperature sensor 141, the humidity sensor 142, the air pressure sensor 143, and the rain sensor 144. The observation data including the radio field intensities and the climatological data acquired by the acquisition unit 111 is correlated with time points (measurement time points) at which the data has been acquired and stored, for example, in a table format (an observation data table) in the storage unit 12.

The input data generating unit 114 generates input data to be input to the precipitable water amount model 121 and the altitudinal water vapor distribution model 122 based on the observation data acquired by the acquisition unit 111. The radio field intensity included in the input data may be expressed as a difference value (sky−bb) obtained by subtracting the radio field intensity (bb) of the black body from the radio field intensity (sky) of the sky.

The input data generating unit 114 may generate input data based on a plurality of pieces of observation data measured at a plurality of time points in a particular time period. Similarly to the training data generating unit 112, the input data generating unit 114 may generate input data by performing a standardization process or a dimension reducing process on the observation data at the plurality of time points.

The input data generating unit 114 inputs the generated input data to the precipitable water amount model 121 and the altitudinal water vapor distribution model 122. In this way, the input data input to the precipitable water amount model 121 and the altitudinal water vapor distribution model 122 may be common.

The precipitable water amount model 121 estimates a precipitable water amount based on the input data input thereto. The altitudinal water vapor distribution model 122 estimates altitude-by-altitude water vapor densities (altitudinal water vapor distribution) based on the input data input thereto.

The output unit 115 converts the precipitable water amount estimated by the precipitable water amount model 121 and the altitude-by-altitude water vapor densities (altitudinal water vapor distribution) estimated by the altitudinal water vapor distribution model 122 to, for example, image data in the form of a graph and outputs the image data to the display device 16. The output unit 115 may convert the precipitable water amounts and the altitude-by-altitude water vapor densities (altitudinal water vapor distributions) at a plurality of successive observation time points to image data in the form of a graph indicating temporal change.

Figure 9:
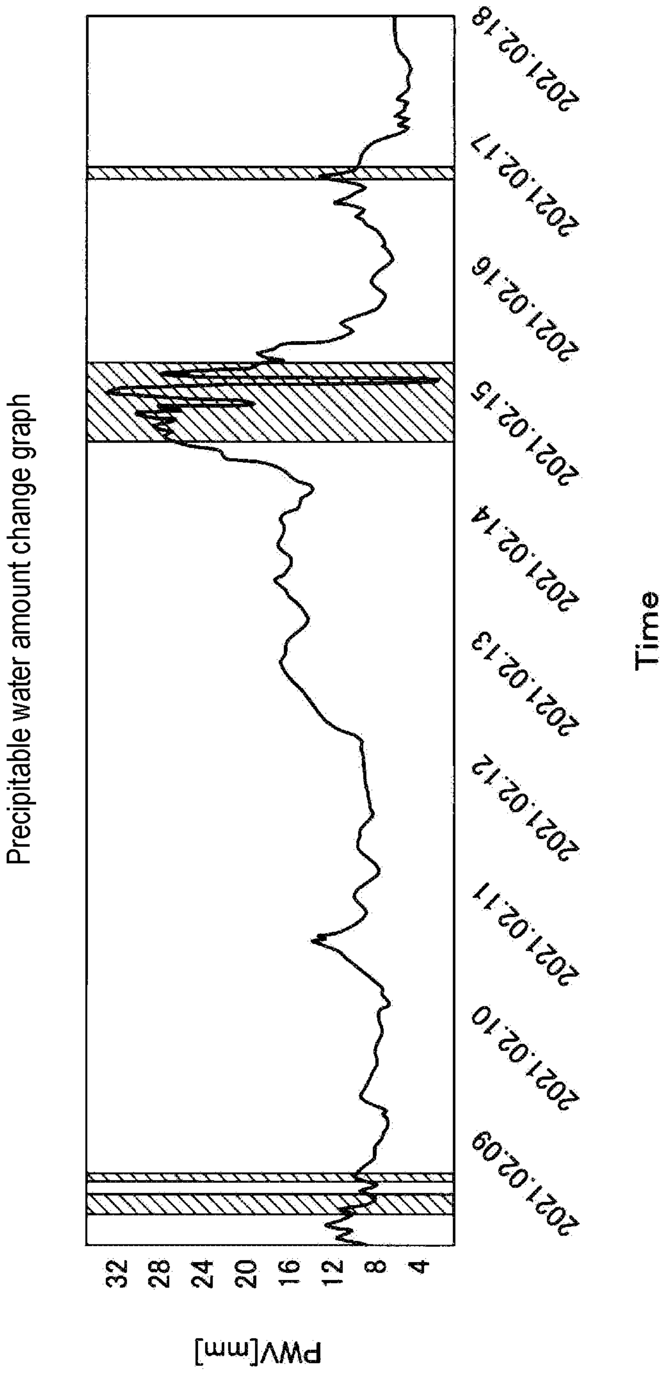
FIG. 9 is an explanatory diagram (a precipitable water amount change graph) illustrating an example of a graphed precipitable water amount change information.

FIG. 9 is an explanatory diagram (a precipitable water amount change graph) illustrating an example of change information of graphed precipitable water amounts. The precipitable water amount change graph is an example of a graph indicating temporal change of the precipitable water amount at a plurality of successive observation time points. The horizontal axis of the precipitable water amount change graph represents the observation time point using the microwave radiometer 1. The vertical axis represents a precipitable water amount (PWV) in the sky (the atmosphere in the vertical direction) at the observation spot using the microwave radiometer 1.

Figure 10:
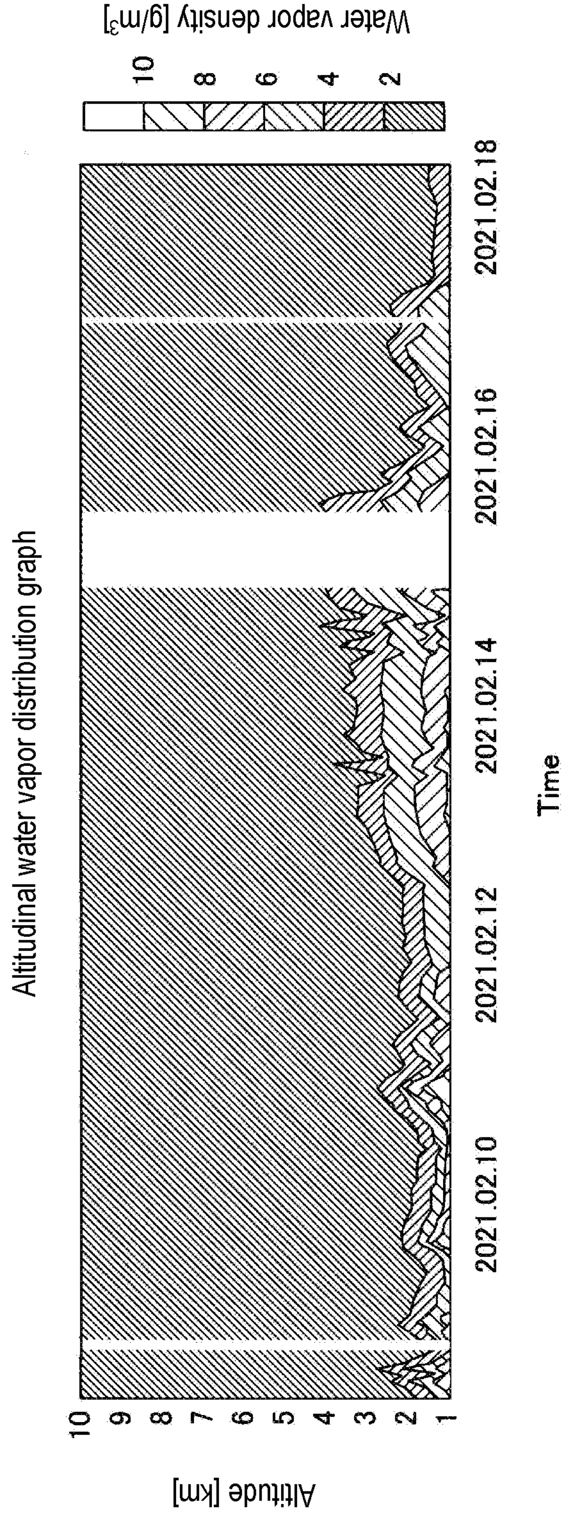
FIG. 10 is an explanatory diagram (an altitudinal water vapor distribution graph) illustrating an example of a graphed altitudinal water vapor distribution.

FIG. 10 is an explanatory diagram (a altitudinal water vapor distribution graph) illustrating an example of a graphed altitudinal water vapor distribution. The altitudinal water vapor distribution graph is an example of a graph indicating temporal change of the altitude-by-altitude water vapor densities (altitudinal water vapor distribution) at a plurality of successive observation time points. The horizontal axis of the altitudinal water vapor distribution graph represents the observation time point using the microwave radiometer 1. The vertical axis represents the altitude of the sky (the atmosphere in the vertical direction) at the observation spot using the microwave radiometer 1. The water vapor density is indicated by a contour diagram in which gradations of color tones vary according to the density.

Figure 11:
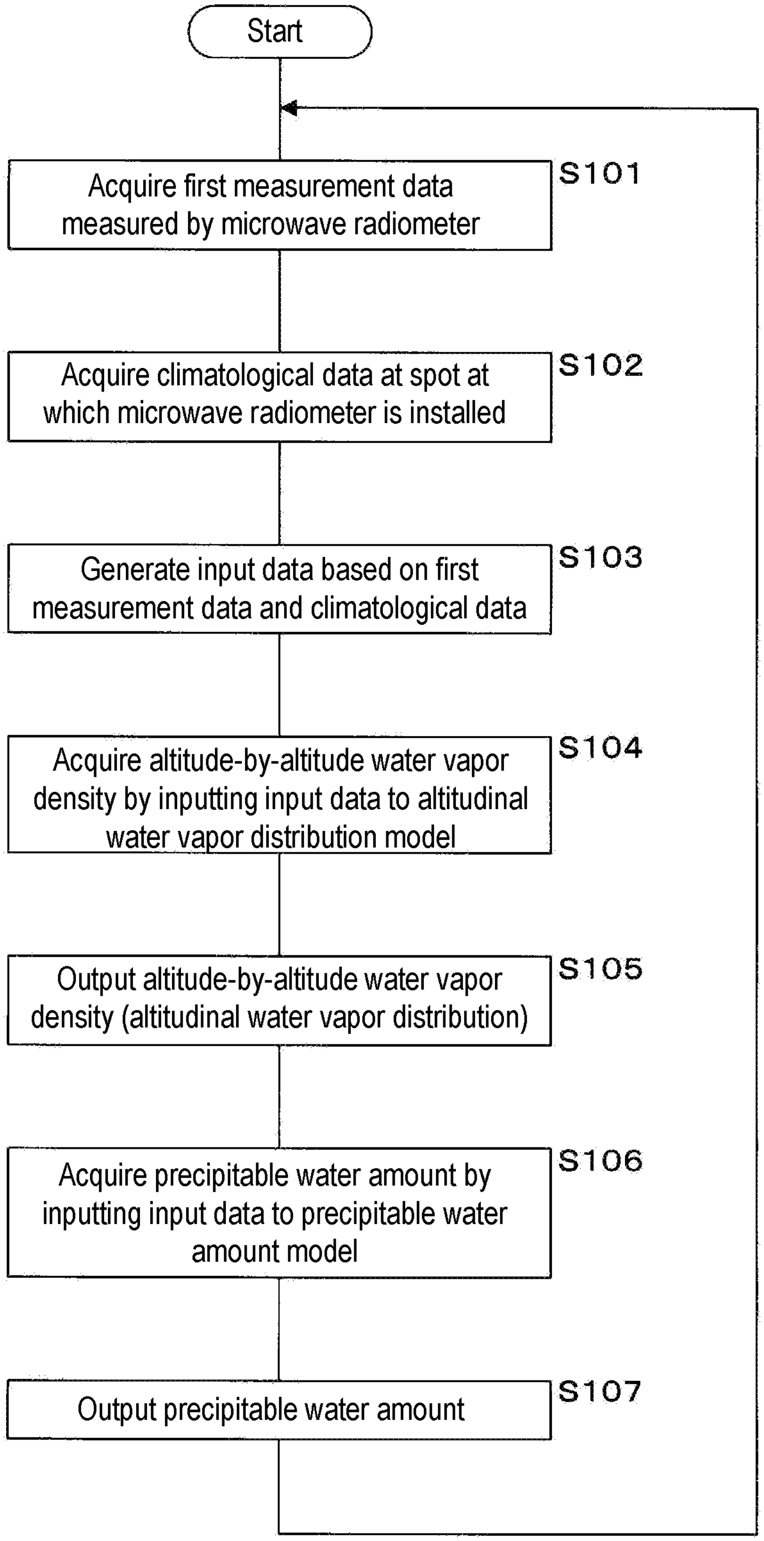
FIG. 11 is a flowchart illustrating an example of a routine (at the time of operating) which is performed by the control unit of the microwave radiometer.

FIG. 11 is a flowchart illustrating an example of a routine (at the time of operating) that is performed by the control unit 11 of the microwave radiometer 1. For example, the control unit 11 of the microwave radiometer 1 receives an operation from an operator via a keyboard connected to the input/output I/F 14 and performs the following processes based on the received operation.

The control unit 11 of the microwave radiometer 1 acquires first measurement data measured by the microwave radiometer 1 (the microwave measuring unit 15) (S101). For example, the control unit 11 of the microwave radiometer 1 acquires climatological data at a spot at which the microwave radiometer 1 is installed (S102). Similarly to the processes of S1 and S2, the control unit 11 of the microwave radiometer 1 performs the processes of S101 and S102.

The control unit 11 of the microwave radiometer 1 generates input data based on the first measurement data and the climatological data (S103). The radio field intensity included in the input data may be expressed as a difference value (sky−bb) obtained by subtracting the radio field intensity (bb) of the black body from the radio field intensity (sky) of the sky. The control unit 11 of the microwave radiometer 1 may generate the input data based on a plurality of pieces of measurement data measured at a plurality of time points in a particular time period. The control unit 11 of the microwave radiometer 1 may generate the input data by performing a standardization process or a dimension reducing process on the observation data at the plurality of time points.

The control unit 11 of the microwave radiometer 1 inputs the input data to the altitudinal water vapor distribution model 122 and acquires altitude-by-altitude water vapor densities (altitudinal water vapor distribution) (S104). The control unit 11 of the microwave radiometer 1 inputs the input data to the altitudinal water vapor distribution model 122 and acquires the altitude-by-altitude water vapor densities (altitudinal water vapor distribution) estimated by the altitudinal water vapor distribution model 122.

The control unit 11 of the microwave radiometer 1 outputs the altitude-by-altitude water vapor densities (altitudinal water vapor distribution) (S105). For example, the control unit 11 of the microwave radiometer 1 graphs information on the altitude-by-altitude water vapor densities (altitudinal water vapor distribution) and outputs the graphed information to the display device 16.

The control unit 11 of the microwave radiometer 1 inputs the input data to the precipitable water amount model 121 and acquires a precipitable water amount (S106). The control unit 11 of the microwave radiometer 1 inputs the input data to the precipitable water amount model 121 and acquires the precipitable water amount estimated by the precipitable water amount model 121.

The control unit 11 of the microwave radiometer 1 outputs the precipitable water amount (S107). For example, the control unit 11 of the microwave radiometer 1 graphs information on the precipitable water amount and outputs the graphed information to the display device 16.

The control unit 11 of the microwave radiometer 1 performs a loop process to perform the routine from S101 again after the process of S107 has been performed. By repeating the processes from S101 to S107 in this way, it is possible to add or update and continue to output information on the precipitable water amount and the altitudinal water vapor distribution changing in a time series based on the successive observation results from the microwave radiometer 1. The control unit 11 of the microwave radiometer 1 may periodically update the graph displayed on the display device 16 by continuing to graph information on the precipitable water amount and the altitudinal water vapor distribution changing in a time series and to output the graphed information to the display device 16. That is, by sequentially inputting a plurality of pieces of input data generated from a plurality of pieces of observation data (the first measurement data and the climatological data) to the learning models (the precipitable water amount model 121 and the altitudinal water vapor distribution model 122), the control unit 11 of the micro wave radiometer 1 can acquire the (a plurality of time-series) precipitable water amounts and the (a plurality of time-series) altitudinal water vapor distributions at a plurality of time points.

In this embodiment, the control unit 11 of the microwave radiometer 1 acquires the radio field intensities (first measurement data) and the climatological data in generating the input data, but is not limited thereto. The control unit 11 of the microwave radiometer 1 may generate input data based on only the radio field intensities (first measurement data) or some of the climatological data such as temperature, humidity, and air pressure in addition to the radio field intensities (first measurement data) and acquire a precipitable water amount and an altitudinal water vapor distribution by inputting the input data to the precipitable water amount model 121 and the altitudinal water vapor distribution model 122.

In this embodiment, training data for training the learning models (precipitable water amount model 121 and the altitudinal water vapor distribution model 122) uses the first measurement data measured by the microwave radiometer 1 as question data and the altitude-by-altitude water vapor densities or the precipitable water amount acquired from the second measurement data measured by the radiosonde as answer data. Accordingly, it is possible to efficiently generate a learning model trained using the second measurement data measured by the radiosonde and to efficiently output the altitude-by-altitude water vapor densities or the precipitable water amount based on the first measurement data measured by the microwave radiometer 1 using the learning model. It is possible to improve measurement accuracy of the first measurement data by using a difference value between a measured value of microwaves from the sky and a measured value of microwaves from a reference radio wave absorber such as a black body as the first measurement data and to improve estimation accuracy of the learning model by using the training data including the first measurement data.

In this embodiment, a plurality of frequencies included in the first measurement data is, for example, about 40 channels (frequencies) in the range of from 16 GHz to 26 GHz, and the radio field intensities (dB) of the 40 channels are stored in the storage unit 12. The control unit 11 can reduce the number of dimensions of the fist measurement data (question data) included in the training data by performing the dimension reducing process on the acquired and stored radio field intensities of the 40 channels, and thus it is possible to achieve a decrease in calculation cost.

In this embodiment, the question data included in the training data includes climatological data at the spot at which the microwave radiometer 1 is installed in addition to the first measurement data measured by the microwave radiometer 1. The climatological data may include at least one of temperature, humidity (absolute humidity or relative humidity), air pressure, and rainfall and may include all the physical quantities. By performing training using the question data, it is possible to improve estimation accuracy of the learning model.

Second Embodiment

Figure 12:
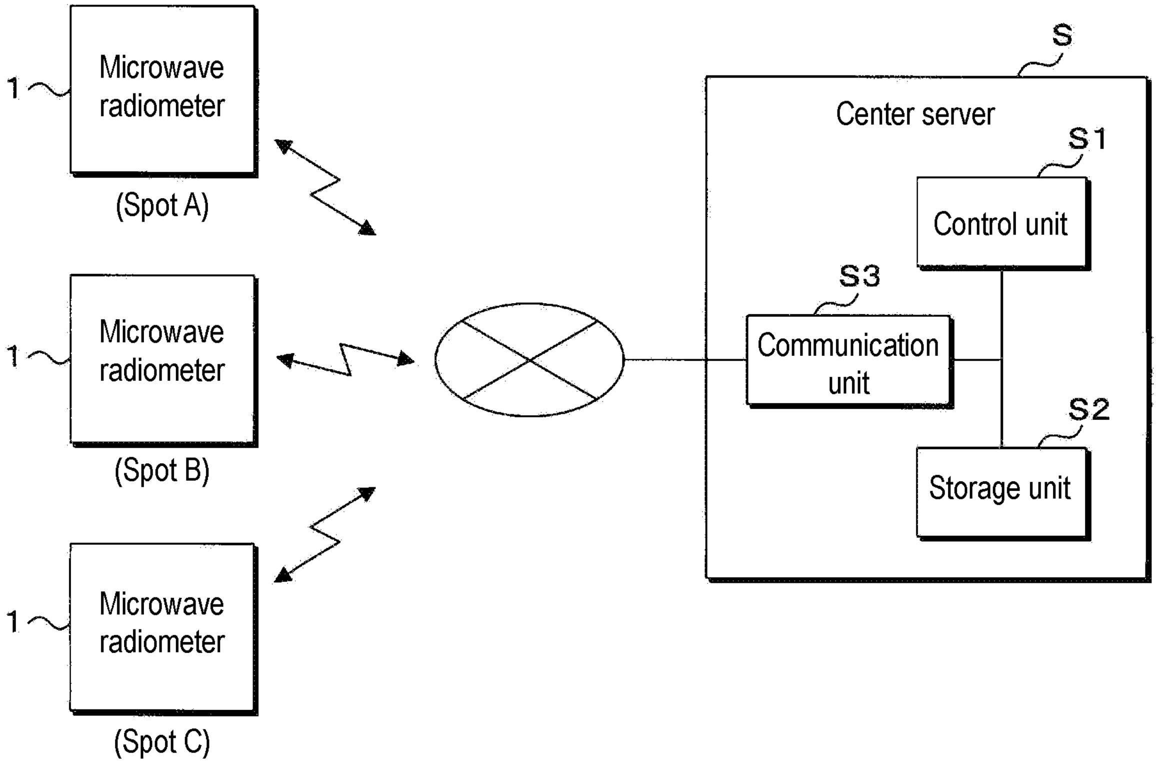
FIG. 12 is a block diagram illustrating an example of a system configuration of a microwave radiometer according to a second embodiment (a plurality of spots).

FIG. 12 is a block diagram illustrating an example of a system configuration of a microwave radiometer 1 according to a second embodiment (at a plurality of spots). In the second embodiment, a water vapor observation system is constituted by a plurality of microwave radiometers 1 installed at different spots and a center server S communicatively connected to the plurality of microwave radiometers 1.

The microwave radiometer 1 according to the second embodiment outputs measured observation data (radio field intensities and climatological data) to the center server S. The center server S is, for example, an information processing device such as a cloud server connected to the Internet and serves as an observation data collection server including a control unit S1, a storage unit S2, and a communication unit S3 and collecting observation data measured (observed) by the plurality of microwave radiometers 1 installed at different spots.

In the storage unit S2 of the center server S, the same precipitable water amount model 121 and the same altitudinal water vapor distribution model 122 as in the first embodiment are stored. Similarly to the control unit 11 of the microwave radiometer 1, the control unit S1 of the center server S generates input data for each spot based on the observation data output (transmitted) from the plurality of microwave radiometer 1 installed at different spots. The control unit S1 of the center server S outputs a precipitable water amount and an altitudinal water vapor distribution for each spot by inputting the generated input data for each spot to the precipitable water amount model 121 and the altitudinal water vapor distribution model 122.

Figure 13:
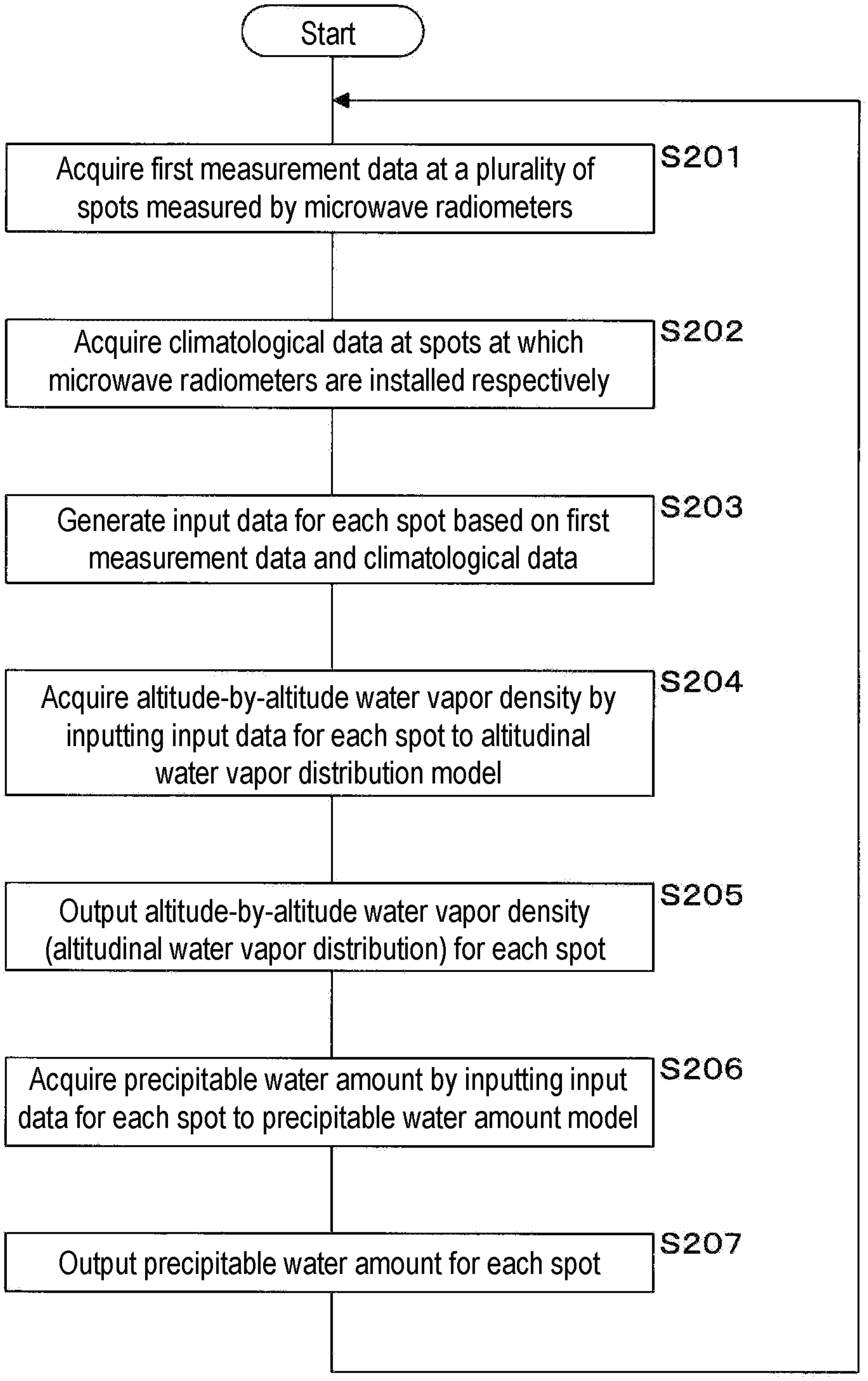
FIG. 13 is a flowchart illustrating an example of a routine which is performed by a control unit of a center server.

FIG. 13 is a flowchart illustrating an example of a routine that is performed by the control unit S1 of the center server S. The center server S performs the following processes normally, for example, when the server starts.

The control unit S1 of the center server S acquires first measurement data at a plurality of spots measured by the microwave radiometers 1 (S201). The control unit S1 of the center server S acquires radio field intensities (first measurement data) at a plurality of spots measured by the microwave radiometers 1 from the microwave radiometers 1 installed at the plurality of spots. Each radio field intensity may be a difference value (sky−bb [dB]) obtained by subtracting the radio field intensity (bb [dB]) of the black body from the radio field intensity (sky [dB]) of the sky.

The control unit S1 of the center server S acquires climatological data at the plurality of spots at which the microwave radiometers 1 are installed (S202). The control unit S1 of the center server S acquires climatological data including temperature, humidity, air pressure, and rainfall at the plurality of spots at which the microwave radiometers 1 are installed from the microwave radiometers 1 installed at the plurality of spots.

The control unit S1 of the center server S generates input data for each spot based on the first measurement data and the climatological data (S203). The control unit S1 of the center server S generates the input data for each spot based on the first measurement data and the climatological data for each spot (for each microwave radiometer 1) similarly to S103.

The control unit S1 of the center server S inputs the input data for each spot to the altitudinal water vapor distribution model 122 and acquires altitude-by-altitude water vapor densities (S204). The control unit S1 of the center server S outputs the altitude-by-altitude water vapor densities (altitudinal water vapor distribution) for each spot (S205). The control unit S1 of the center server S inputs the input data for each spot to the precipitable water amount model 121 and acquires a precipitable water amount (S206). The control unit S1 of the center server S outputs the precipitable water amount for each spot (S207). The control unit S1 of the center server S performs the processes of S204 to S207 on the input data for each spot (for each microwave radiometer 1) similarly to the processes of S104 to S107. Similarly to the first embodiment, the control unit S1 of the center server S performs a loop process to perform the routine from S201 again after the process of S207 has been performed.

FIG. 14 is an explanatory diagram illustrating an example of an observation state (superimposed in map information) at a plurality of spots. The explanatory diagram (a multiple-spot multiple-view screen) is an example of screen data output from the center server S. The center server S acquires map information for identifying a plurality of spots at which a plurality of microwave radiometer 1 is installed, causes the altitude-by-altitude water vapor densities or the precipitable water amount at each of the plurality of spots on the acquired map information, and outputs the resultant information to the display device 16, a mobile terminal, or the like.

The multiple-spot multiple-view screen includes a map area in which the map information for identifying the spots at which the plurality of microwave radiometers 1 is installed and a list display area in which observation data measured (observed) by the microwave radiometers 1 is displayed in the form of a list. In the map area, the spots at which the microwave radiometers 1 are installed are displayed by a diagram, and the altitude-by-altitude water vapor densities and the precipitable water amount measured at each spot are superimposed and displayed. In the list display area, a list of radio field intensities and altitude-by-altitude water vapor densities measured at the spots is displayed. In the list display area, a button, an icon, or the like for which a hyperlink is set may be disposed, and a child screen for displaying a precipitable water amount change graph or an altitudinal water vapor distribution graph at a selected spot may be displayed in a pop-up manner by clicking the button or the like. By clicking the button or the like, a child screen for displaying a graph (a radio field intensity change graph) indicating temporal change of the radio field intensity (sky−bb) at the selected spot may be displayed in a pop-up manner.

In this embodiment, the control unit S1 of the center server S acquires observation data (first measurement data and climatological data) for each spot measured at each of a plurality of spots at which the microwave radiometers 1 are installed by radio communication, inputs the observation data for each spot to the learning models (the altitudinal water vapor distribution model 122 and the precipitable water amount model 121), and outputs altitude-by-altitude water vapor densities (altitudinal water vapor distribution) or a precipitable water amount for each of the plurality of spots. Since the control unit S1 of the center server S provides the altitude-by-altitude water vapor densities (altitudinal water vapor distribution) or the precipitable water amount for each spot in the form of a table, a graph, or the like for the purpose of enabling comparison and outputs the information to, for example, a mobile terminal via the communication unit S3, it is possible to efficiently provide the information to a weather relevant person or the like.

It should be understood that the above-described embodiments are examples in all respects and are not restrictive. The technical features described in the embodiments can be combined, and it is intended that the scope of the invention includes all modifications in the appended claims and scopes equivalent to the claims.

Terminology

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processor. A processor can be a microprocessor, but in the alternative, the processor can be a controller, microcontroller, or state machine, combinations of the same, or the like. A processor can include electrical circuitry configured to process computer-executable instructions. In another embodiment, a processor includes an application specific integrated circuit (ASIC), a field programmable gate array (FPGA) or other programmable device that performs logic operations without processing computer-executable instructions. A processor can also be implemented as a combination of computing devices, e.g., a combination of a digital signal processor (DSP) and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C. The same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

It will be understood by those within the art that, in general, terms used herein, are generally intended as "open" terms (e.g., the term "including" should be interpreted as "including but not limited to," the term "having" should be interpreted as "having at least," the term "includes" should be interpreted as "includes but is not limited to," etc.).

For expository purposes, the term "horizontal" as used herein is defined as a plane parallel to the plane or surface of the floor of the area in which the system being described is used or the method being described is performed, regardless of its orientation. The term "floor" can be interchanged with the term "ground" or "water surface". The term "vertical" refers to a direction perpendicular to the horizontal as just defined. Terms such as "above," "below," "bottom," "top," "side," "higher," "lower," "upper," "over," and "under," are defined with respect to the horizontal plane.

As used herein, the terms "attached," "connected," "mated," and other such relational terms should be construed, unless otherwise noted, to include removable, moveable, fixed, adjustable, and/or releasable connections or attachments. The connections/attachments can include direct connections and/or connections having intermediate structure between the two components discussed.

Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of the stated amount. Features of embodiments disclosed herein preceded by a term such as "approximately", "about", and "substantially" as used herein represent the feature with some variability that still performs a desired function or achieves a desired result for that feature.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A non-transitory computer-readable recording medium, recording a program causing a computer to perform:

measuring, by a microwave radiometer, a first measurement data, the first measurement data includes radio field intensity data for radio waves of a lower limit frequency, an upper limit frequency, and frequencies between the lower limit frequency and the upper limit frequency;

wherein the radio waves of the frequencies between the lower limit frequency and the upper limit frequency include a peak frequency that is a peak of the radio field intensites of radio waves radiated from water vapor;

outputting altitude-by-altitude water vapor densities or a precipitable water vapor amount by inputting the first measurement data to a trained model which outputs the altitude-by-altitude water vapor densities or the precipitable water vapor amount when the first measurement data is input, wherein a plurality of pieces of the first measurement data measured at a plurality of time points by the microwave radiometer are acquired; and further comprising:

generating change information of an altitudinal water vapor distribution based on the respective altitude-by-altitude water vapor densities at the plurality of time points output from the trained model; and outputting the change information of the altitudinal water vapor distribution.

2. The non-transient computer-readable recording medium according to claim 1, wherein the first measurement data includes a radio wave intensity for each of a plurality of frequencies.

3. The non-transient computer-readable recording medium according to claim 2, wherein a dimension reduction process is performed on the radio wave intensity for each of the plurality of frequencies included in the first measurement data, and the first measurement data including the radio wave intensity subjected to the dimension reduction process is input to the trained model.

4. The non-transient computer-readable recording medium according to claim 1, wherein the trained model is trained using training data including the altitude-by-altitude water vapor densities or the precipitable water vapor amount acquired from second measurement data measured by a radiosonde and the first measurement data.

5. The non-transient computer-readable recording medium according to claim 4, wherein the training data further includes climatological data including temperature, humidity, air pressure, or rainfall at a spot at which the microwave radiometer is installed, and further comprising:

outputting the altitude-by-altitude water vapor densities or the precipitable water vapor amount by inputting the first measurement data and the climatological data to the trained model.

6. The non-transient computer-readable recording medium according to claim 1, wherein the plurality of pieces of the first measurement data measured at the plurality of time points by the microwave radiometer are acquired; and further comprising:

generating change information of the precipitable water vapor amount based on the precipitable water vapor amount at the plurality of time points output from the trained model; and outputting the change information of the precipitable water vapor amount.

7. The non-transient computer-readable recording medium according to claim 3, wherein the trained model is trained using training data including the altitude-by-altitude water vapor densities or the precipitable water vapor amount acquired from second measurement data measured by a radiosonde and the first measurement data.

8. The non-transient computer-readable recording medium according to claim 7, wherein the training data further includes climatological data including temperature, humidity, air pressure, or rainfall at a spot at which the microwave radiometer is installed, and further comprising:

outputting the altitude-by-altitude water vapor densities or the precipitable water vapor amount by inputting the first measurement data and the climatological data to the trained model.

9. The non-transient computer-readable recording medium according to claim 8, wherein a plurality of pieces of the first measurement data measured at a plurality of time points by the microwave radiometer are acquired; and further comprising:

generating change information of a precipitable water vapor amount based on the precipitable water vapor amount at the plurality of time points output from the trained model; and outputting the change information of the precipitable water vapor amount.

10. The non-transient computer-readable recording medium according to claim 9, wherein first measurement data for each spot measured by the respective microwave radiometers installed in a plurality of spots is acquired; and further comprising:

outputting the altitude-by-altitude water vapor densities or the precipitable water vapor amount at each of the plurality of spots by inputting the first measurement data for each spot to the trained model.

11. The non-transient computer-readable recording medium according to claim 10, wherein map information for identifying the plurality of spots at which the plurality of microwave radiometers is installed is acquired; and further comprising:

superimposing the altitude-by-altitude water vapor densities or the precipitable water vapor amount at each of the plurality of spots in the map information.

12. The non-transient computer-readable recording medium according to claim 11, wherein climatological data including temperature, humidity, air pressure, or rainfall at each of the plurality of spots at which the plurality of microwave radiometers is installed is acquired; and further comprising:

inputting the first measurement data and the climatological data for each of the plurality of spots to the trained model.

13. A non-transitory computer-readable recording medium, recording a program causing a computer to perform:

measuring, by a microwave radiometer, a first measurement data, the first measurement data includes radio field intensity data for radio waves of a lower limit frequency, an upper limit frequency, and frequencies between the lower limit frequency and the upper limit frequency;

wherein the radio waves of the frequencies between the lower limit frequency and the upper limit frequency include a peak frequency that is a peak of the radio field intensites of radio waves radiated from water vapor;

outputting altitude-by-altitude water vapor densities or a precipitable water vapor amount by inputting the first measurement data to a trained model which outputs the altitude-by-altitude water vapor densities or the precipitable water vapor amount when the first measurement data is input, wherein a plurality of pieces of the first measurement data measured at a plurality of time points by the microwave radiometer are acquired; and further comprising:

generating change information of the precipitable water vapor amount based on the precipitable water vapor amount at the plurality of time points output from the trained model; and outputting the change information of the precipitable water vapor amount, wherein first measurement data for each spot measured by the respective microwave radiometers installed in a plurality of spots is acquired; and further comprising:

outputting the altitude-by-altitude water vapor densities or the precipitable water vapor amount at each of the plurality of spots by inputting the first measurement data for each spot to the trained model.

14. The non-transient computer-readable recording medium according to claim 13, wherein map information for identifying the plurality of spots at which the plurality of microwave radiometers is installed is acquired; and further comprising:

superimposing the altitude-by-altitude water vapor densities or the precipitable water vapor amount at each of the plurality of spots in the map information.

15. The non-transient computer-readable recording medium according to claim 13, wherein climatological data including temperature, humidity, air pressure, or rainfall at each of the plurality of spots at which the plurality of microwave radiometers is installed is acquired; and further comprising:

inputting the first measurement data and the climatological data for each of the plurality of spots to the trained model.

16. An estimation method that is performed by a computer, comprising:

measuring, by a microwave radiometer, a first measurement data, the first measurement data includes radio field intensity data for radio waves of a lower limit frequency, an upper limit frequency, and frequencies between the lower limit frequency and the upper limit frequency;

wherein the radio waves of the frequencies between the lower limit frequency and the upper limit frequency include a peak frequency that is a peak of the radio field intensites of radio waves radiated from water vapor;

outputting altitude-by-altitude water vapor densities or a precipitable water vapor amount by inputting the first measurement data to a trained model which outputs the altitude-by-altitude water vapor densities or the precipitable water vapor amount when the first measurement data is input, wherein a plurality of pieces of the first measurement data measured at a plurality of time points by the microwave radiometer are acquired; and further comprising:

generating change information of an altitudinal water vapor distribution based on the respective altitude-by-altitude water vapor densities at the plurality of time points output from the trained model; and outputting the change information of the altitudinal water vapor distribution.

17. The estimation method according to claim 16, wherein the first measurement data includes a radio wave intensity for each of a plurality of frequencies.

18. The estimation method according to claim 17, wherein a dimension reduction process is performed on the radio wave intensity for each of the plurality of frequencies included in the first measurement data, and the first measurement data including the radio wave intensity subjected to the dimension reduction process is input to the trained model.

19. An estimation method that is performed by a computer, comprising:

measuring, by a microwave radiometer, a first measurement data, the first measurement data includes radio field intensity data for radio waves of a lower limit frequency, an upper limit frequency, and frequencies between the lower limit frequency and the upper limit frequency;

wherein the radio waves of the frequencies between the lower limit frequency and the upper limit frequency include a peak frequency that is a peak of the radio field intensites of radio waves radiated from water vapor;

outputting altitude-by-altitude water vapor densities or a precipitable water vapor amount by inputting the first measurement data to a trained model which outputs the altitude-by-altitude water vapor densities or the precipitable water vapor amount when the first measurement data is input, wherein a plurality of pieces of the first measurement data measured at a plurality of time points by the microwave radiometer are acquired; and further comprising:

generating change information of the precipitable water vapor amount based on the precipitable water vapor amount at the plurality of time points output from the trained model; and outputting the change information of the precipitable water vapor amount, wherein first measurement data for each spot measured by the respective microwave radiometers installed in a plurality of spots is acquired; and further comprising:

outputting the altitude-by-altitude water vapor densities or the precipitable water vapor amount at each of the plurality of spots by inputting the first measurement data for each spot to the trained model.

20. The estimation method according to claim 19, wherein map information for identifying the plurality of spots at which the plurality of microwave radiometers is installed is acquired; and further comprising:

superimposing the altitude-by-altitude water vapor densities or the precipitable water vapor amount at each of the plurality of spots in the map information.

21. The estimation method according to claim 19, wherein climatological data including temperature, humidity, air pressure, or rainfall at each of the plurality of spots at which the plurality of microwave radiometers is installed is acquired; and further comprising:

inputting the first measurement data and the climatological data for each of the plurality of spots to the trained model.

* * * * *